United States Patent
Li et al.

(10) Patent No.: US 10,900,031 B2
(45) Date of Patent: Jan. 26, 2021

(54) METHOD FOR CONSTRUCTING HIGH-RESOLUTION SINGLE CELL HI-C LIBRARY WITH A LOT OF INFORMATION

(71) Applicants: NANJING ANNOROAD GENE TECHNOLOGY CO., LTD, Nanjing (CN); ANNOROAD GENE TECHNOLOGY (BEIJING) CO., LTD, Beijing (CN)

(72) Inventors: Xiaolin Li, Beijing (CN); Jiezhong Zhang, Beijing (CN); Hongmei Zhao, Beijing (CN); Zhihua Pei, Beijing (CN); Zhaoling Xuan, Beijing (CN); Dawei Li, Beijing (CN); Junbin Liang, Beijing (CN); Chongjian Chen, Beijing (CN)

(73) Assignees: ZHEJIANG ANNOROAD BIO-TECHNOLOGY CO. LTD., Yiwu (CN); ANNOROAD GENE TECHNOLOGY (BEIJING) CO., LTD., Beijing (CN)

( * ) Notice: Subject to any disclaimer, the term of this patent is extended or adjusted under 35 U.S.C. 154(b) by 0 days.

(21) Appl. No.: 15/769,073

(22) PCT Filed: Oct. 19, 2015

(86) PCT No.: PCT/CN2015/092181
§ 371 (c)(1),
(2) Date: Apr. 18, 2018

(87) PCT Pub. No.: WO2017/066908
PCT Pub. Date: Apr. 27, 2017

(65) Prior Publication Data
US 2018/0305685 A1 Oct. 25, 2018

(51) Int. Cl.
*C12N 15/10* (2006.01)
*C40B 50/06* (2006.01)
*C12Q 1/68* (2018.01)
*C12Q 1/6806* (2018.01)
*C12Q 1/686* (2018.01)
*C40B 40/06* (2006.01)

(52) U.S. Cl.
CPC .......... *C12N 15/1093* (2013.01); *C12Q 1/68* (2013.01); *C12Q 1/6806* (2013.01); *C40B 50/06* (2013.01); *C12Q 1/686* (2013.01); *C40B 40/06* (2013.01)

(58) Field of Classification Search
CPC ...... C12N 15/1093; C12Q 1/68; C12Q 1/686; C40B 50/06; C40B 40/06
See application file for complete search history.

(56) References Cited

FOREIGN PATENT DOCUMENTS

| WO | WO 2012/005595 A2 | 1/2012 |
|---|---|---|
| WO | WO2015071748 | 5/2016 |

OTHER PUBLICATIONS de Bourcy et al. ("A Quantitative Comparison of Single-Cell Whole Genome Amplification Methods" PLoS ONE 9(8): e105585, pp. 1-9).*
Hijun Duan et al, "A genome-wide 3C-method for characterizing the three-dimensional architectures of genomes", Methods, (Nov. 1, 2012), vol. 58, No. 3, doi:10.1016/j.ymeth.2012.06.018, ISSN 1046-2023, pp. 277-288, XP055110280 [X] 1-6, 10 * p. 4-pp. 4, 5.

* cited by examiner

*Primary Examiner* — Robert H Havlin
(74) *Attorney, Agent, or Firm* — Adam Warwick Bell; Matthew Rupert Kaser; Joseph Curtis Edmonson

(57) ABSTRACT

Provided in the present invention is a method for constructing a high-resolution single cell Hi-C library with a large amount of information, comprising the following steps: Step B: obtain a small amount of fixed chromatin; Step C: digest the fixed chromatin in Step B to obtain fragments of the fixed chromatin; Step D: reconnect the fragments of the fixed chromatin in Step C directly to obtain reconnected fragments of the fixed chromatin; Step E: de-fix the reconnected fragments of the fixed chromatin in Step D to release DNA fragments; Step F: amplify the released DNA fragments in Step E to obtain amplified products; and Step H: construct a sequencing DNA library by using the amplified products as the DNA fragments to be sequenced.

16 Claims, No Drawings

METHOD FOR CONSTRUCTING HIGH-RESOLUTION SINGLE CELL HI-C LIBRARY WITH A LOT OF INFORMATION

FIELD OF THE INVENTION

The invention relates to a method for constructing a library to capture the three-dimensional structure of chromatin in whole genome scale, which relates to the field of gene sequencing technology.

BACKGROUND OF THE INVENTION

DNA carries the genetic information of a cell, which exists in the form of chromatin in each cell of an organism, and controls the entire process of life. Currently, most of the research on DNA information is regarding the base sequence within DNA molecule (one dimensional information of DNA), and explores the principle of life activity by analyzing the base arrangement information.

The real state of the nucleus is a tiny three-dimensional space, the DNA molecular with linear structure locates in nucleus in a complex folding way, so that the original one-dimensional DNA sequences are endowed with three-dimensional conformation, and which lead to a large number of complicated gene regulation mode. In this regard, the simple one dimensional DNA sequences information cannot provide real information about the real spatial distribution of DNA and therefore cannot explain a series of gene regulation phenomena caused by the spatial conformation.

To solve this problem, there are a series of testing methods such as the 3c (chromosome conformation capture) technique and derived 4c, 5c techniques. These techniques are based on sequencing as the basic detection means, and use nuclear proteins to form factors fixing DNA structure, then construct DNA sequences with spatial structure information by DNA fragments reconnection, and finally detect the chromatin DNA information by sequencing technique and calculate the spatial distribution and interaction thereof. Although these techniques can provide part interaction information of the chromatin to a certain extent, due to the approaches and technical limitations, they can only detect specific sites or pan of the DNA interaction sites, but cannot explore the three dimensional interaction information at the level of the whole nucleus. Therefore, a large amount of information will be missed inevitably. However, this is especially important for discovering unknown interaction information.

With the advent of high-throughput sequencing technologies in recent years, the acquisition of large-scale genomic information becomes easier. Hi-C technology combines high-throughput sequencing and detects the chromatin information throughout the whole nucleus. Hi-C is a derivative technique of chromosome conformation capture (Referred to as 3C), which refers to the capture of chromosome conformation based on high-throughput sequencing. It captures the spatial interactions between different gene loci in a genome-wide and studies DNA elements that regulate genes in three dimensions.

For example, Patent Reference 1 and Non-Patent Reference 1 report a Hi-C method which uses formaldehyde to fix the chromatin structure, and then the original genomic sequence is interrupted by restriction enzymes and labeled with biotin, followed by reconnecting into new DNA molecules with structure information. In this process, if two DNA fragments of different genomic positions are linked to form a hybrid molecule, this will be considered as a proof that these two DNA molecules are spatially close to each other. The DNA is then purified and broken up, and the tagged biotin molecules are captured and enriched for desired DNA hybrid molecules with spatial interaction information. Finally, a high-throughput sequencing library is constructed and sequenced by paired-end sequencing to obtain the information about the spatial interaction of the whole chromatin. The method mainly includes the following steps: 1) first of all, a sample with not less than $10^6$ cells is fixed by formaldehyde cross-linking to cross-link the DNA molecules which are close to each other in the interior space, and then the cells are collected; 2) the cells are lysed in a lysis system in combination with grinding to obtain the isolated nucleus; 3) chromatin of the cross-linked cells is digested with restriction enzymes (such as EcoRI); 4) the digested ends are labeled with biotin to form blunt ends; 5) the blunt ends are ligated by DNA ligase, and DNA fragments within the same cross-linked molecule will have a greater probability to form new molecules together; 6) the cross-linking is reversed by high temperature treatment (65° C.) to release double-stranded DNA molecules; 7) un-linked terminal biotin labels are removed; 8) the DNA is fragmented and biotin captured and the regions with connected sites of the hybrid molecules are enriched; and 9) a Illumina sequencing library is constructed and double-stranded sequencing is performed to obtain data.

However, the method starts with a large sample size of not less than $10^6$ cells and uses extensive grinding and extraction methods through the whole process, and is not suitable for small samples (up to $10^5$ cells) especially for Hi-C detection at a single cell level. In addition, regarding to a large number of cell samples, this method can only detect the overall chromatin conformation of the cell population, but cannot detect and compare the difference of chromatin conformation between individuals.

In another aspect, Non-Patent Reference 2 reports a single cell Hi-C method, which starts with a large sample size of $10^6$ as well. The pretreatment uses formaldehyde to fix the chromatin structure, then breaks down the original genomic sequence by restriction enzyme followed by biotin labeling, and then reconnects the fragments to form a new DNA molecule with structural information. In this process, if two DNA fragments of different genomic positions are linked to form a hybrid molecule, this will be considered as a proof that the two DNA molecules are spatially close to each other. Next, the pre-treated nucleus is picked under a microscope to obtain a single nucleus, then for the single nuclear sample, cross-linking is removed, biotin is captured and DNA is fragmented by restriction enzymes, and enriched and obtain desired DNA hybrid molecules with spatial interaction. Finally, a high-throughput sequencing library is constructed and detected by paired-end sequencing to obtain the spatial interaction information about the chromatin. The method mainly comprises the following steps: 1) first of all, a sample with not less than $10^6$ cells is fixed by formaldehyde cross-linking to cross-link DNA molecules which are close to each other in the interior space, and then the cells are collected; 2) the cells are lysed in a lysis system in combination with grinding to obtain the isolated nucleus; 3) chromatin of the cross-linked cells is digested with restriction enzymes (such as EcoRI); 4) the digested ends are labeled by biotin to form blunt ends; 5) the blunt ends are ligated by DNA ligase, and DNA fragments within the same cross-linked molecule will have a greater probability to form a new molecule together; 6) a single cell nucleus is picked under microscope to obtain a single nucleus sample with Hi-C treatment; 7) the formaldehyde cross-linking is removed by high temperature treatment to release DNA; 8) the DNA is biotin captured and the regions with connected sites of the hybrid molecules are enriched; 9) the DNA is fragmented by a second restriction enzyme so as to be adapted to be the size for Illumina sequencing library insert fragments; 10) a Illumina sequencing library is constructed with magnetic beads conjugated with biotin-labeled fragments (hybrid molecules of fragments with spatial interaction) as a vector and subjected to paired-end sequencing to obtain data.

Although this method operates on a single nucleus at a later stage for de-cross linking and library construction, and eventually provides the Hi-C result at the single cell level, in the early treatment stage, due to the need to rely on bulky formaldehyde cross-linking treatment and grinding and breaking cells to obtain the nucleus, the method still requires a large sample size of not less than $10^6$ cells at the starting point for Hi-C treatment. Therefore, it does not really achieve the single cell level Hi-C test at the first beginning, and cannot be applied to small samples ($10^5$ cells or less), especially single-cell samples. Furthermore, since the method undergoes multiple steps such as restriction enzyme digestion, terminal repair, biotin labeling, blunt end ligation, biotin capture, and adapter adding before library amplification, and these steps are carried out on a set of genomic copy, the efficiency of each of the step may affect the information captured finally, resulting in serious loss of information throughout the experiment and low number of interacted DNA fragments finally captured. In addition, since this method employs two kinds of restriction enzymes for chromatin digestion and reconnected product fragmentation, respectively. In order to ensure the fragmentation efficiency of the reconnected product, the endonucleases used in this step are much more frequently found in the genome than the frequencies of endonucleases used in chromatin digestion. This causes inability of this method to perform chromatin digestion with the 4-base enzyme present at high frequencies in the genome, ultimately resulting in lower resolution of the obtained Hi-C library data. Non-Patent Reference 2 also attempts to perform chromatin digestion using the 4-base enzyme present in the genome at a high frequency, but the resolution and amount of information cannot be improved since subsequent reconnected products cannot be fragmented by any endonuclease with high-frequency. Moreover, the way to study a single cell in this method is to select a single nucleus, the difficulty of its operation and the requirements of the instrument, technology are much higher than picking a single cell.

Therefore, none of the above Hi-C methods in the prior art is a practical Hi-C method that can be applied to a single cell or small numbers of cells.

Patent Reference 1

International Publication No. WO2010036323A1

Non-Patent Reference 1

Lieberman-Aiden E et al. Comprehensive mapping of long-range interactions reveals folding principles of the human genome. Science 326, 289-293 (2009)

Non-Patent Reference 2

Takashi Nagano et al. Single-cell Hi-C reveals cell-to-cell variability in chromosome structure. Nature 502, 59-64 (2013)

SUMMARY OF THE INVENTION

In view of the above shortcomings in the prior art, an object of the present invention is to provide a method for constructing a Hi-C library that can be applied to a small amount of chromatin (a small amount of cells or even a single cell chromatin).

The present inventors conducted in-depth research to solve the above technical problems, and made ingenious improvements on the basis of the traditional method for constructing a Hi-C library and provide a Hi-C library construction method apply to a small amount of chromatin for the first time so as to achieve the present invention.

The invention relates to:

1. A method for constructing a Hi-C library, and the method comprises the following steps:
    Step B: obtain a small amount of fixed (i.e. treated) chromatin;
    Step C: digest the fixed chromatin in Step B to obtain fragments of the fixed chromatin;
    Step D: reconnect the fragments of the fixed chromatin in Step C directly to obtain reconnected fragments of the fixed chromatin;
    Step E: de-fix the reconnected fragments of the fixed chromatin in Step D to release DNA fragments;
    Step F: amplify the released DNA fragments in Step E to obtain amplification products; and
    Step H: construct a sequencing DNA library by using the amplification products as the DNA fragments to be sequenced.

2. The method of item 1, wherein the small amount of fixed chromatin is $10^{-6}$~$10^2$ ng chromatin in terms of naked DNA.

3. The method of item 1 or item 2, wherein the small amount of fixed chromatin is $10^{-5}$~10 ng chromatin in terms of naked DNA.

4. The method of one of the items 1 to 3, wherein a deoxyribonuclease is used in Step C to digest the fixed chromatin.

5. The method of item 4, wherein the deoxyribonuclease is Type I restriction enzyme, Type II restriction enzyme, or Type III restriction enzyme.

6. The method of one of the items 1 to 5, wherein a sticky end or blunt end ligation method is applied in Step D to reconnect the fragments of the fixed chromatin obtained in Step C.

7. The method of one of the items 1 to 6, further comprising: Step G: the amplification product in Step F is fragmented to obtain DNA fragments with smaller size: and
    in Step H, the DNA fragments with smaller size obtained in Step G is used as the DNA fragments to be sequenced to construct a sequencing DNA library.

8. The method of item 7, wherein ultrasonic interruption method, transposase method, endonuclease method or hydraulic shear method is used in Step G to fragment the amplification product.

9. The method of item 8, wherein the size of the smaller DNA in Step G is 50~1000 bp.

10. The method of any one of items 1 to 9, further comprising:
    Step A: obtain a small amount of cells with fixed chromatin; and
    in Step B, the cells obtained in Step A is lysed to obtain a small amount of fixed chromatin.

11. The method of item 10, wherein the small amount of cells with fixed chromatin is 1~10000 cells.

12. The method of item 10, wherein the small amount of cells with fixed chromatin is 1~1000 cells.

13. The method of item 10, wherein the small amount of cells with fixed chromatin is a single cell.

14. The method of item 10, wherein the Step A comprises:

Step A-1: fix the chromatin of a certain amount of cells to obtain a certain amount of cells with fixed chromatin; and Step A-2: pick a small amount of cells with fixed chromatin from the certain amount cells with fixed chromatin obtained in Step A-1

15. The method of item 10, wherein the Step A comprises:

Step A-3: fix the chromatin of a small amount of cells to obtain a small amount of cells with fixed chromatin.

16. A method for detecting chromatin regions with potential spatial interaction, and the method comprises:

construct the Hi-C library by the method of any one of items 1-15; and sequence all or part of the Hi-C library and align the obtained information with the primary sequence information of chromatin DNA.

Effect of the Invention

According to the present invention, there is provided a method for constructing a Hi-C library which is characterized in a small initial sample size, high resolution, large volume of information, and easy operation.

The methods in prior art cannot process trace samples and single cell samples. However, the present invention can start with a single cell or trace sample (1-1000 cells) from the first step, which solves the problem, i.e., the Hi-C detection is hard to conduct from cells with small sample size.

The methods in prior art cannot detect the single cell chromatin conformation. However, the invention can perform Hi-C analysis on a single cell and detect and study the chromatin conformation of the individual cell, as well as the differences of chromatin conformation between different cells.

In order to solve the problem of large loss of DNA interaction information in the prior art, the present invention abandons the steps such as end-repair after digestion, biotin labeling and capture, and the like, and the blunt end ligation is replaced by the sticky end ligation which has higher efficiency so as to decrease the loss of the amount of information and capture more chromatin conformation information.

The methods in prior art obtain low resolution of chromatin conformation. However, the invention adopts a method of random interruption when the library is fragmented, and the fragmentation effect thereof is much better than that of restriction enzyme digestion. This operation allows choosing restriction enzymes with higher resolution such as 4-base sequence recognition restriction enzymes for chromatin digestion, resulting in higher resolution of chromatin conformation.

In the prior art, it is difficult to pick a single nucleus, however, the present invention can select a single cell for library construction, which is less difficult than picking a single cell nucleus.

DETAILED DESCRIPTION OF THE INVENTION

The technical and scientific terms mentioned in this specification have the same meanings as commonly understood by a person skilled in the art and in case of conflict, the present specification is defined.

In one aspect, the invention provides a method for constructing a Hi-C library (the method of the invention), and the method comprises the following steps:

Step B: obtain a small amount of fixed (i.e. treated) chromatin;

Step C: digest the fixed chromatin in Step B to obtain fragments of the fixed chromatin;

Step D: reconnect the fragments of the fixed chromatin in Step C directly to obtain reconnected fragments of the fixed chromatin;

Step E: de-fix the reconnected fragments of the fixed chromatin in Step D to release DNA fragments;

Step F: amplify the released DNA fragments in Step E to obtain amplification products; and Step H: construct a sequencing DNA library by using the amplification products as the DNA fragments to be sequenced.

Preferably, the method of the invention further comprises:

Step G: the amplification product in Step F is fragmented to obtain DNA fragments with smaller size; and in Step H, the DNA fragments with smaller size obtained in Step G is used as the DNA fragments to be sequenced to construct a sequencing DNA library.

The method of the invention also comprises:

Step A: obtain a small amount of cells with fixed chromatin; and in Step B, the cells obtained in Step A is lysed to obtain a small amount of fixed chromatin.

There are no particular limitations on the manner for obtaining a small amount of cells with fixed chromatin in Step A, for example, a certain amount of the chromatin of cells can be fixed first to obtain a certain amount of cells with fixed chromatin, and then a small amount of cells with fixed chromatin can be selected from the certain amount of cells with fixed chromatin; or the chromatin of a small amount of cells can be fixed directly to obtain a small amount of cells with fixed chromatin. It should be noted that the cells here may also be the nucleus.

In this specification, Hi-C refers to three-dimensional interaction group of the chromatin, which is a method to capture a genome-wide chromatin conformation and study the three dimensional structure of chromatin and the spatial relationship between different DNA regions. Hi-C library refers to a DNA library for high throughput sequencing to obtain possible chromatin interaction information by high throughput sequencing in Hi-C method.

Herein, "a small amount of chromatin" refers to an amount of chromatin which cannot be operated by the prior Hi-C methods. Generally, it refers to the chromatin of 1~10000 cells, or the chromatin of 1~1000 cells, or the chromatin of 1~100 cells, or even the chromatin of one cell (single cell), or even part of the chromatin of one cell (single cell). As calculated by mass, the "small amount of chromatin" can be $10^{-6}$~$10^2$ ng, preferably 10~10 ng in terms of naked DNA.

In the present description, "a small amount of cells" refers to an amount of cells which cannot be operated by the prior Hi-C methods. Generally, it refers to 1~10000 cells, or 1~1000 cells, or 1~100 cells, or even one cell (single cell).

In the present description, "fix", "fixing" or "fixation" refers to the portions of the chromatin close to each other in three dimensional space are fixed in a state close to the natural conformation. In this description, the chromatin also includes chromosomal morphology. The fixation normally can be performed by cross-linking of proteins on chromatin. Methods for cross-linking of protein on chromatin are known to the skilled person in the art, for example, ultra-violet rays or chemical reagents such as tetranitromethane, carbodiimides, formaldehyde, methanol, ethanol, valeraldehyde, nitrogen mustard, dimethyl sulfuric acid, formaldehyde release agent, imide esters, mitomycin C, mustard gas and psoralen can be used alone, or the chemical reagents can be used in combination with ultraviolet rays to achieve the cross-linking. For example, in the case by using formaldehyde to cross link so as to fixation, cells can be made into cell suspension droplets in an appropriate amount (eg. 1-10000000 μL) of water, TE buffer, physiological saline, PBS or cell culture medium, then a suitable amount (for example, 1~10000000 μL) of formaldehyde solution (the concentration thereof is not limited, and may be, for example, 1 to 20 wt %) is added, and the mixture is allowed to stand at room temperature for a certain period of time (for example, 1-100 min) to effect cross-linking. Then, a certain amount of amino acid (one amino acid or a mixture of multiple amino acids) or protein (such as BSA and the like) is added to the reaction droplet to terminate the cross-linking reaction.

In Step A, chromatin of a certain amount of cells (for example, $10^5$ or more, preferably $10^6$ to $10^8$) can be fixed to obtain a certain amount of cells with fixed chromatin, then a small amount of cells with fixed chromatin is picked; or the chromatin of a small amount of cells is fixed directly to obtain the small amount of cells with fixed chromatin. The small amount of cells can be picked by capillary, dilution, gradient dilution or flow cytometry.

In Step B, cells obtained in Step A are lysed to obtain the fixed chromatin. Cell lysis can generally be performed by placing the cells in a suitable cell lysis buffer. The formula and amount of the cell lysis buffer can be appropriately determined by those skilled in the art according to the type and amount of the cells.

In Step C, the fixed chromatin obtained in Step B is digested to obtain the fixed chromatin fragment. The digestion can be performed by using a DNase. As the DNase, type I restriction enzyme, type II restriction enzyme or type III restriction enzyme is preferred. In the Hi-C method recited in Non-Patent Reference 2, since the subsequent steps require to use restriction enzyme that recognize 4-base sequence to carry out the DNA fragmentation, only recognizing 6-base sequence restriction enzyme can be used to digest the chromatin. This way of digestion has low resolution, which only keeps a small amount of information. In another aspect, in the method of the present invention, ultrasound interruption method, transposase method and hydraulic shear method and the like can be employed in subsequent steps to make the DNA fragment, and the recognizing 4-base sequence restriction enzyme or other nuclease with higher resolution can be used in Step C to digest the chromatin. Theoretically, it can increase the resolution by more than 10 times, resulting in significant increase the amount of chromatin interaction information obtained. Of course, a restriction enzyme that recognizes a 6-base sequence can also be used for chromatin digestion in Step C.

In Step D, the fixed chromatin fragments obtained in Step C is reconnected directly to obtain the reconnected fixed chromatin fragments. Here, "reconnect directly" or "reconnect . . . directly" refers to reconnect the fragments without biotin labeling on the fixed chromatin fragments. In addition, when chromatin digestion is performed by using the sticky end restriction enzymes in Step C, the fixed chromatin fragments obtained will have sticky ends, and preferably, the invention does not include modification of the sticky ends into blunt ends, instead, it employs the sticky ends ligation method to reconnect the chromatin fragments, which gives a better efficiency than the sticky ends ligation. Of course, the method of the present invention can also employ modified blunt ends for ligation (without ligation site labeling such as adding nucleotide with biotin labeling for modification of sticky ends) or use blunt end restriction enzyme to digest and then employ blunt end ligation. The ligation can be performed by using DNA ligase with terminal ligation activity, such as T4 DNA ligase, T3 DNA ligase, *E. coli* DNA ligase, thermostable DNA ligase and the like. The amount of the enzyme and substrate used in the ligation reaction, as well as the reaction conditions, can be suitably selected by those skilled in the art as needed. For example, the ligation can be carried out usually in 0.1 to 10× ligase buffer at 0 to 80° C. (preferably 10 to 40° C.) for about 1 minute to 200 hours (preferably 1 to 30 hours).

In Step E, the reconnected fixed chromatin fragments obtained in Step D are de-fixed to release the DNA fragments. In the description, "de-fixed" refers to release the fixed state of the portions close to each other in three dimensional space in the fixed chromatin fragments. For example, when the fixation is achieved by cross-linking of protein on chromatin, "de-fix" means to remove the cross-linking of the protein. The method for removing the cross-linking of the protein is known to the skilled person in the art, including methods by using biological, chemical treatment cross-link removal methods and/or high temperature cross-link removal methods to release the DNA fragments. For example, as the method to treat cross-linking with high temperature, the protein can be de-cross linked by placing the above system after ligation reaction at 50~100t (preferably 60~80° C.) for 1 minute to 200 hours (preferably 1-30 hours) after ligation. As the method to treat the cross-linking by biological, chemical methods, endopeptidase, serine protease, thiol protease, metalloprotease, aspartic protease, pepsin, trypsin, cathepsin, papain, subtilisin, proteinase K, DTT, NaCl, KCl or the combination thereof can be added to the above system. Of course, biological, chemical and high temperature cross-link removal treatments can also be combined for protein de-cross linking. Moreover, in the case that high temperature treatment is employed in Step F for DNA fragments amplification, Step E can be performed together with Step F.

In Step F, the DNA fragments released in Step E are amplified to obtain the amplification products. The amplification method is not particularly limited as long as a sufficient amount (for example, 0.001 to 1000 ng) of the amplification products to achieve a DNA library for sequencing can be obtained. For example, amplification methods suitable for a small number of cells, single cells or trace DNAs such as MDA, MALBAC, NEB-WGA, GenomePlex (preferably MALBAC) can be used. The specific conditions of these amplification methods can be appropriately selected by those skilled in the art as needed. The amplification method described above can normally be carried out on the basis of a PCR reaction (polymerase chain reaction) which is generally carried out by a certain PCR reaction procedure (temperature cycle). The PCR reaction procedure generally includes steps of denaturation, annealing, extension and the like. The design of the primers used in the PCR reaction is well-known to those skilled in the art and can be performed, for example, according to the "Molecular Cloning: A Laboratory Manual" (by J. Sambrook, et al., Translated by Huang Peitang, 3rd ed., 2005), or use computer software (such as Primer Premier 6.0 developed by Premier) to design.

In Step G, the amplified products obtained in Step F are fragmented to obtain smaller DNA fragments. In the present specification, "smaller DNA fragments" refers to a DNA library of a size suitable for sequencing (eg, second generation sequencing, third generation sequencing, or fourth generation sequencing), such as an Illumina DNA sequencing library. The specific size of "smaller DNA fragments" may be, for example, 10 to 50,000 bp, preferably 50 to 1,000 bp. In the Hi-C method described in Non-Patent Reference 2, amplification products fragmentation is only suitably performed by using a restriction enzyme that recognizes a 4-base sequence. However, in the method of the present invention, it is also possible to use ultrasonic interruption method, transposase method, hydraulic shearing method to fragment the amplified products. This improves resolution and gives more information. Techniques for fragmenting the amplified products using above methods are known to those skilled in the art and appropriate conditions can be selected as appropriate.

In Step H, a DNA library for sequencing is constructed by using smaller DNA fragments obtained in Step G as the DNA fragments to be sequenced. The sequencing DNA library may be constructed by using methods for constructing a small DNA fragments library, for example, the standard Illumina small DNA fragment library construction method, the PCR free method, the one-step method, and the like. Various methods for constructing DNA sequencing libraries are known to those skilled in the art and can be performed by those skilled in the art according to routine operation. For example, methods for constructing standard Illumina small DNA fragments construction method typically include the steps of end repairing, adding A at the end, adapter ligation, amplification, purification of amplification products and the like, following Illumina's recommended protocol.

It should be noted that, in the above steps C G, part of the products can be taken for the next step as needed.

By sequencing all or part of the DNA library constructed by the method of the present invention and aligning the sequence with chromatin DNA primary sequence information, it is possible to obtain information on chromatin regions that may spatially interact with each other.

EXAMPLES

The present invention will be further described in detail with reference to the following examples. It should be understood that the specific embodiments described herein are used for explaining the present invention, rather than limiting the present invention.

Example 1

1. Sample Treatment
1.1 Cross-Linking
  1.1.1 1 10 human leukocyte samples were placed in 10 μL PBS to prepare cell suspension droplets;
  1.1.2 Add 100 μL 4% formaldehyde solution for cross-linking, and the reaction was allowed to stand at room temperature for 5 min;
  1.1.3 5 μL glycine solution of 0.25 M was added to the reaction droplet to terminate cross-linking. The reaction was allowed to stand at room temperature for 5 min, then ice bath for 15 min.
1.2 Picking a Single Cell (a Small Amount of Cells)
  A single cell or a small amount of cells were picked by capillary method and treated with lysis buffer.
Formula of the lysis buffer:
10 mM Tris-HCl pH 7.4
30 mM NaCl
0.2% NP-40
10% protease inhibitor cocktail
Sterile water
2. Cell lysis
  2.1 The cell lysis buffer with the single cell sample was micro-centrifuged to pool the liquid at the bottom of the tube, followed by keeping in an ice bath for 45 min;
  2.2 4% SDS solution was added to the system for a final concentration of 0.35% SDS and followed by keeping in 37° C. warm bath for 60 min;
  2.3 20% Triton X-100 solution was added to the system for a final concentration of 3% Triton X-100, and followed by keeping in 37° C. warm bath for 60 min.
3. Chromatin Digestion
  3.1 For each sample, 8U (International Units) of Mbo I and a final concentration of 1× NEBuffer 3.1 were added, and followed by keeping in 37° C. warm bath for 16 hours.
  3.2 The endonuclease was inactivated by keeping in warm bath at 65° C. for 20 min.
4. DNA Reconnection and DNA, Protein De-Cross Linking.
  4.1 For each sample, 8 U (International Units) T4 DNA ligase and ligase buffer at a final concentration of 1× were added, and followed by keeping in 16° C. warm bath for 16 hours.
  4.2 Kept in 65° C. warm bath for 16 hours.
5. DNA Amplification
  By using the Yikon single cell whole genome-wide amplification kit based on the MALBAC method, the sample obtained above was subjected to DNA amplification according to the instruction of the kit to obtain the amplification products of the reconnected DNA.
6. DNA Fragmentation
  The amplification product was fragmented through sonication by using a Diagenode Bioruptor UCD-600 (NGS) with a procedure of: 30 seconds ultrasound, 30 seconds rest, 22 cycles. The previously amplified DNA fragments were fragmented into DNA fragments between 100 and 700 bp in size.
7. Small Fragments Library Construction
7.1 End Repair
  End repair reaction system was added to the products obtained from the previous step according to the table below:

| | |
|---|---|
| Fragmented DNA Sample | 75 μL |
| 10 × PNK buffer | 10 μL |
| dNTP Solution Set (10 mM) | 4 μL |
| T4 DNA Polymerase | 5 μL |
| T4 Polynucleotide Kinase | 5 μL |
| Klenow Fragment | 1 μL |
| Total volume | 100 μL |

The sample was placed into Thermomixer in warm bath at 20° C. for 30 min. After the reaction, the DNA in reaction system was recovered and purified by using Beckman Agencourt AMPure XP nucleic acid purification kit and dissolved in 32 μL of water.
7.2 Adding "A" to the End
  "A" reaction system was added to the products obtained from the previous steps according to the table below:

| | |
|---|---|
| Sample from the previous step | 32 μL |
| 10 × blue buffer | 5 μL |

-continued

| | |
|---|---|
| dATP (1 mM) | 10 μL |
| Klenow (3'-5'exo-) | 3 μL |
| Total volume | 50 μL |

The sample was placed in Thermomixer in warm bath at 3° C. for 30 min. The DNA in the reaction system was recovered and purified by using Beckman Agencourt AMPure XP Nucleic Acid Purification Kit and dissolved in 18 μL of water.

7.3 "Adapter" Ligation:

The "Adapter" reaction system was added to the products obtained from the previous steps according to the table below:

| | |
|---|---|
| Sample from the previous step | 18 μL |
| 2 × Rapid ligation Buffer | 25 μL |
| PE Index Adapter | 2 μL |
| T4 DNA Ligase | 5 μL |
| Total volume | 50 μL |

The sample was placed in Thermomixer in warm bath at 20° C. for 15 min. The DNA in the reaction system was recovered and purified by using Beckman Agencourt AMPure XP Nucleic Acid Purification Kit and dissolved in 30 μL of water.

7.4 Library Amplification

The following reaction system was added to the products obtained from the previous steps according to the table below:

| | |
|---|---|
| Purified sample after adding Adapter | XμL |
| Index-X (10 pmol/μL) | 2 μL |
| Ann Common Primer (10 pmol/μL) | 2 μL |
| HiFi DNA Polymerase Mix | 25 μL |
| ddH$_2$O | (21-X) μL |
| Total volume | 50 μL |

The PCR reaction program was set as follows:

| | |
|---|---|
| 94° C. | 3 min |
| 94° C. | 15 s |
| 63° C. | 30 s |
| 72° C. | 30 s |
| 72° C. | 5 min |
| 4° C. | ∞ |

(94° C. 15 s, 63° C. 30 s, 72° C. 30 s) 10 cycles

The purification was performed by using a Beckman Agencourt AMPure XP Nucleic Acid Purification Kit; dissolved in 15 μL of water; and the DNA concentration was determined after purification.

7.5 Quality Check of the Library, Paired-End Sequencing on the Machine, Obtaining the Data.

Unlike the non-patent reference 1 and 2, the present invention does not use biotin to capture the reconnected sites DNA fragments, but use informatics analysis to filter out the fragments in which the non-reconnected sites are located.

Because filtering these fragments already exists in standard Hi-C sequencing data analysis method (the filtering condition in Non-Patent Reference 1 and 2 is to remove the fragments with biotin labeling in the library which are not reconnected), the library of the present invention does not require additional filtering condition to perform bioinformatics analysis to obtain the interaction information of chromosome in three-dimension.

7.6 Obtaining the Information Amount Obtained and Comparing with the Single Cell Nucleus Hi-C in Prior Art.

The present invention performs chromatin digestion by using Mbo I (recognition site is GATC but sensitive to Dam, Dcm and CpG methylation), at the sequencing amount of 14M-19M paired-end sequencing reads, the number of interaction pairs between the captured chromatin regions is 270-331K.

In contrast, in Non-Patent Reference 2, chromatin digestion was performed by using Dpn II in the single cell nucleus Hi-C (the recognition site is also GATC but sensitive to Dam, Dcm methylation, that is, the recognition sites should be more than those of Mho I, therefore, in theory, more information should be obtained on the interaction between the digested fragments and chromatin regions), at the sequencing amount of 13M paired-end sequencing reads, the number of interaction pairs between the captured chromatin regions is only 12K. The remaining single nucleus in Non-Patent Reference 2 were subjected to chromatin digestion with Bgl II endonuclease, at the sequencing amount of 5.5M-15.3M paired-end sequencing reads, the number of interaction pairs between the captured chromatin regions is 11.7k-30.6k. The chromatin conformational information obtained with the present invention is significantly higher than that of the single cell nucleus Hi-C method in Non-Patent Reference 2.

| | Single cell nucleus Hi-C method (Non-Patent Reference 2) | | The present invention |
|---|---|---|---|
| Chromatin digestive enzymes | Dpn II | Bgl II | Mbo I |
| Sequencing amount | 13M | 5.5-15.3M | 14-19M |
| Number of interaction pairs between the captured chromatin | 12K | 11.7-30.6K | 270-331K |

It should also be noted that combinations of any one of the technical features or technical features described as an integral part of a certain technical solution in the present specification may also be applied to the embodiments that are practicable and are not inconsistent with the spirit of the present invention Other technical solutions. In addition, the technical features described as components of different technical solutions may also be combined in any manner to form other technical solutions without any departure from the gist of the present invention. The present invention also includes the technical solutions obtained by combination in the above cases, and these technical solutions are equivalent to those described in the present specification.

The above description shows and describes the preferred embodiments of the present invention. As mentioned before, it should be understood that the present invention is not limited to the forms disclosed herein, and should not be considered as an exclusion of other embodiments but may be applied to various other combinations, modifications, and environments. Modifications can be made to the above teachings or techniques or knowledge in the related art within the scope of the inventive concept described herein. Modifications and variations made by those skilled in the art without departing from the spirit and scope of the present invention should fall within the protection scope of the appended claims of the present invention.

INDUSTRIAL APPLICABILITY

According to the present invention, the detection of chromatin conformations can be performed on a cells sample with small amount. Cell types include, but are not limited to, animal cells, plant cells, microbial cells, viruses, cancer cells; the sources of these cells include, but are not limited to, primary cultures, cell line cultures, tissues, organisms, environmental sources, fossils.

According to the present invention, the difference in chromosomal conformation between different cells can be compared. The differences among these cells include, but are not limited to, different species sources, different organ sources, different cell types, different cell cycles, different developmental stages, different culture conditions, different treatment conditions, different individual cells.

According to the present invention, it is possible to analyze the relationship between changes in the intracellular chromatin conformation and changes in other DNA, RNA, and protein. These changes include, but are not limited to, the following: DNA mutations, DNA methylation changes, gene knockouts, gene knockins, transgenes, RNA expression changes, RNA silencing, microRNA expression changes, long noncoding RNA expression changes, 16s rDNA changes, mRNA expression changes, ribosomal RNA expression changes, RNA conformational changes, DNA conformation changes, DNA regulatory elements changes, chromosomal abnormalities, chromosome deletions, chromosomal duplication, chromosomal aberrations, chromosome confirmation changes, CNV, protein expression changes, antigen and antibody changes, secreted protein changes, membrane protein changes.

According to the present invention, it is possible to study the relationship between the chromatin conformation of a cell and specific genes, DNA, RNA, and protein and to analyze the interaction between a specific protein in a cell and DNA and RNA in a nucleus.

In accordance with the present invention, the cell properties or functions as well as the chromatin conformation, DNA, RNA and protein functions can be studied in conjunction with other methods for studying DNA, RNA, and protein. These other methods for studying DNA, RNA, and proteins include, but are not limited to: microarray, QPCR, first generation sequencing, second generation sequencing, third generation sequencing, fourth generation sequencing, gene sequencing, genomic sequencing, metagenomic sequencing, exon sequencing, intron sequencing, target gene capture sequencing, RNA sequencing, expression profile sequencing, transcriptome sequencing, small RNA transcriptome, microRNA sequencing, macro transcriptome sequencing, LncRNA sequencing, tumor gene sequencing, tumor genome sequencing, Bisulfite methylation sequencing, ChIP-DNA sequencing, MeDIP sequencing, RRBS sequencing, Target-BS sequencing, hmC sequencing.

What is claimed is:

1. A method for constructing a Hi-C library covering a whole genome, wherein the Hi-C library is a DNA library for high throughput sequencing to obtain possible chromatin interaction information by high throughput sequencing in Hi-C method and Hi-C method is a method to capture a genome-wide chromatin conformation and study the three dimensional structure of chromatin and the spatial relationship between different DNA regions, and the Hi-C method for constructing the Hi-C library comprises the following steps:
   Step A: obtaining a small number of cells with fixed chromatin, wherein the small amount of cells with fixed chromatin is 1~10000 cells;
   Step B: lysing of the cells obtained in Step A to obtain a small amount of fixed chromatin, wherein the small amount of fixed chromatin is $10^{-6}$~$10^2$ ng chromatin in terms of naked DNA;
   Step C: digesting the fixed chromatin in Step B to obtain fragments of the fixed chromatin;
   Step D: reconnecting the fragments of the fixed chromatin without biotin labeling on the fixed chromatin fragments in Step C directly to obtain reconnected fragments of the fixed chromatin;
   Step E: de-fixing the reconnected fragments of the fixed chromatin in Step D to release DNA fragments;
   Step F: amplifying the released DNA fragments in Step E using a whole genome amplification method to obtain amplification products, wherein the used amplification method is capable of amplifying $10^{-6}$~$10^2$ ng chromatin in terms of naked DNA, and the amplification method is MDA, MALBAC, NEB-WGA or GenomePlex;
   Step G: the amplification product in Step F is fragmented to obtain DNA fragments with smaller size; and
   Step H: constructing a sequencing DNA library by using the amplification products as the DNA fragments to be sequenced, in Step H, the DNA fragments with smaller size obtained in Step G is used as the DNA fragments to be sequenced to construct a sequencing DNA library.

2. The method of claim 1, wherein the small amount of fixed chromatin is $10^{-5}$~10ng chromatin in terms of naked DNA.

3. The method of claim 1, wherein a deoxyribonuclease is used in Step C to digest the fixed chromatin.

4. The method of claim 3, wherein the deoxyribonuclease is Type I restriction enzyme, Type II restriction enzyme, or Type III restriction enzyme.

5. The method of claim 1, wherein a sticky end or blunt end method is applied in Step D to reconnect the fragments of the fixed chromatin obtained in Step C.

6. The method of claim 1, wherein ultrasonic interruption method, transposase method, endonuclease method or hydraulic shear method is used in Step G to fragment the amplification product.

7. The method of claim 6, wherein the size of the smaller DNA in Step G is 50~1000 bp.

8. The method of claim 1, wherein the small amount of cells with fixed chromatin is 1~1000 cells.

9. The method of claim 1, wherein the small amount of cells with fixed chromatin is a single cell.

10. The method of claim 1, wherein the Step A comprises:
    Step A-1: fix the chromatin of a certain amount of cells to obtain a certain amount of cells with fixed chromatin; and
    Step A-2: pick a small amount of cells with fixed chromatin from the certain amount cells with fixed chromatin obtained in Step A-1.

11. The method of claim 1, wherein the Step A comprises:
    Step A-3: fix the chromatin of a small amount of cells to obtain a small amount of cells with fixed chromatin.

12. A method for detecting chromatin regions with potential spatial interaction, wherein the method comprises:
    constructing the Hi-C library by the method of claim 1; and sequencing all or part of the Hi-C library and align the obtained information with the primary sequence of chromatin DNA.

13. The method of claim 12, wherein a deoxyribonuclease is used in Step C to digest the fixed chromatin and wherein the deoxyribonuclease is Type I restriction enzyme, Type II restriction enzyme, or Type III restriction enzyme.

14. The method of claim 12, further comprising:
Step G: the amplification product in Step F is fragmented to obtain DNA fragments with smaller size; and
in Step H, the DNA fragments with smaller size obtained in Step G is used as the DNA fragments to be sequenced to construct a sequencing DNA library.

15. The method of claim 12 further comprising:
Step A: obtain a small amount of cells with fixed chromatin; and
in Step B, the cells obtained in Step A is lysed to obtain a small amount of fixed chromatin.

16. The method of claim 11, wherein the small amount of cells with fixed chromatin is a single cell.

* * * * *